US008761870B2

(12) United States Patent
McGree et al.

(10) Patent No.: US 8,761,870 B2
(45) Date of Patent: Jun. 24, 2014

(54) IMPEDANCE MEASUREMENTS

(75) Inventors: James Matthew McGree, The Gap (AU); Stephen Brent Duffull, Forest Lake (AU); Leigh Cordwin Ward, Kenmore Hills (AU); John Anthony Eccleston, St Lucia (AU)

(73) Assignee: Impedimed Limited, Pinkenba, Queensland (AU)

( * ) Notice: Subject to any disclaimer, the term of this patent is extended or adjusted under 35 U.S.C. 154(b) by 1514 days.

(21) Appl. No.: 12/302,914

(22) PCT Filed: May 25, 2007

(86) PCT No.: PCT/AU2007/000726
§ 371 (c)(1),
(2), (4) Date: Nov. 23, 2009

(87) PCT Pub. No.: WO2007/137333
PCT Pub. Date: Dec. 6, 2007

(65) Prior Publication Data
US 2010/0087750 A1    Apr. 8, 2010

(30) Foreign Application Priority Data

May 30, 2006  (AU) ................ 2006902907

(51) Int. Cl.
*A61B 5/05* (2006.01)
(52) U.S. Cl.
USPC ...................................... 600/547
(58) Field of Classification Search
USPC ...................................... 600/547
See application file for complete search history.

(56) References Cited

U.S. PATENT DOCUMENTS

| 3,316,896 | A | 5/1967 | Thomasset |
| 3,834,374 | A | 9/1974 | Ensanian et al. |
| 3,851,641 | A | 12/1974 | Toole et al. |
| 3,871,359 | A | 3/1975 | Pacela |
| 4,008,712 | A | 2/1977 | Nyboer |
| 4,034,854 | A | 7/1977 | Bevilacqua |
| 4,144,878 | A | 3/1979 | Wheeler |
| RE30,101 | E | 9/1979 | Kubicek et al. |
| 4,184,486 | A | 1/1980 | Papa |
| 4,291,708 | A | 9/1981 | Frei et al. |
| 4,314,563 | A | 2/1982 | Wheeler |

(Continued)

FOREIGN PATENT DOCUMENTS

| CA | 2231038 A1 | 11/1999 |
| CA | 2613524 A1 | 1/2007 |

(Continued)

OTHER PUBLICATIONS

Liu et al., Primary Multi-frequency Data Analyze in Electrical Impedance Scanning, Proceedings of the IEEE-EMBS 2005, 27th Annual Int'l Conference of the Engineering in Med. and Biology Soc., Shanghai, China, Sep. 4, 2005; 1504-1507.

(Continued)

*Primary Examiner* — Max Hindenburg
*Assistant Examiner* — Adam Eiseman
(74) *Attorney, Agent, or Firm* — Hahn & Voight PLLC; Roger C. Hahn

(57) ABSTRACT

A method of determining frequencies for use in performing impedance measurements. The method includes determining estimates for parameter values representing an impedance response for at least one subject, using the estimated parameter values to determine a design and using the design to determine frequencies for use in impedance measurements.

6 Claims, 6 Drawing Sheets

(56) References Cited

U.S. PATENT DOCUMENTS

| | | |
|---|---|---|
| 4,353,372 A | 10/1982 | Ayer |
| 4,365,634 A | 12/1982 | Bare et al. |
| 4,401,356 A | 8/1983 | Bare |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,646,754 A | 3/1987 | Seale |
| 4,686,477 A | 8/1987 | Givens et al. |
| 4,688,580 A | 8/1987 | Ko et al. |
| 4,695,955 A | 9/1987 | Faisandier |
| 4,763,660 A | 8/1988 | Kroll et al. |
| 4,793,362 A | 12/1988 | Tedner |
| 4,832,608 A | 5/1989 | Kroll |
| 4,890,630 A | 1/1990 | Kroll et al. |
| 4,895,163 A | 1/1990 | Libke et al. |
| 4,905,705 A | 3/1990 | Kizakevich et al. |
| 4,911,175 A | 3/1990 | Shizgal |
| 4,924,875 A | 5/1990 | Chamoun |
| 4,942,880 A | 7/1990 | Slovak |
| 4,951,682 A | 8/1990 | Petre |
| 5,025,784 A | 6/1991 | Shao et al. |
| 5,063,937 A | 11/1991 | Ezenwa et al. |
| 5,078,134 A | 1/1992 | Heilman et al. |
| 5,086,781 A | 2/1992 | Bookspan |
| 5,101,828 A | 4/1992 | Welkowitz et al. |
| 5,143,079 A | 9/1992 | Frei et al. |
| 5,197,479 A | 3/1993 | Hubelbank et al. |
| 5,199,432 A | 4/1993 | Quedens et al. |
| 5,246,008 A | 9/1993 | Mueller |
| 5,280,429 A | 1/1994 | Withers |
| 5,305,192 A | 4/1994 | Bonte et al. |
| 5,309,917 A | 5/1994 | Wang et al. |
| 5,311,878 A | 5/1994 | Brown et al. |
| 5,372,141 A | 12/1994 | Gallup et al. |
| 5,415,164 A | 5/1995 | Faupel et al. |
| 5,421,344 A | 6/1995 | Popp |
| 5,423,326 A | 6/1995 | Wang et al. |
| 5,449,000 A | 9/1995 | Libke et al. |
| 5,454,377 A | 10/1995 | Dzwonczyk et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A | 4/1996 | Reining |
| 5,511,553 A | 4/1996 | Segalowitz |
| 5,526,808 A | 6/1996 | Kaminsky |
| 5,529,072 A | 6/1996 | Sramek |
| 5,544,662 A | 8/1996 | Saulnier et al. |
| 5,557,242 A | 9/1996 | Wetherell |
| 5,562,607 A | 10/1996 | Gyory |
| 5,588,429 A | 12/1996 | Isaacson et al. |
| 5,596,283 A | 1/1997 | Mellitz et al. |
| 5,626,146 A | 5/1997 | Barber et al. |
| 5,679,022 A | 10/1997 | Cappa et al. |
| 5,704,355 A | 1/1998 | Bridges |
| 5,718,231 A | 2/1998 | Dewhurst et al. |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,876,353 A | 3/1999 | Riff |
| 5,906,614 A | 5/1999 | Stern et al. |
| 5,919,142 A | 7/1999 | Boone et al. |
| 5,957,861 A | 9/1999 | Combs et al. |
| 6,006,125 A | 12/1999 | Kelly et al. |
| 6,011,992 A | 1/2000 | Hubbard et al. |
| 6,015,389 A | 1/2000 | Brown |
| 6,018,677 A | 1/2000 | Vidrine et al. |
| 6,026,323 A | 2/2000 | Skladnev et al. |
| 6,122,544 A | 9/2000 | Organ |
| 6,125,297 A | 9/2000 | Siconolfi |
| 6,142,949 A | 11/2000 | Ubby |
| 6,151,520 A | 11/2000 | Combs |
| 6,151,523 A | 11/2000 | Ferrer et al. |
| 6,173,003 B1 | 1/2001 | Whikehart et al. |
| 6,208,890 B1 | 3/2001 | Sarrazin et al. |
| 6,228,033 B1 | 5/2001 | Koobi et al. |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,256,532 B1 | 7/2001 | Cha |
| 6,292,690 B1 | 9/2001 | Petrucelli et al. |
| 6,339,722 B1 | 1/2002 | Heethaar et al. |
| 6,354,996 B1 | 3/2002 | Drinan et al. |
| 6,469,732 B1 | 10/2002 | Chang et al. |
| 6,472,888 B2 | 10/2002 | Oguma et al. |
| 6,496,725 B2 | 12/2002 | Kamada et al. |
| 6,497,659 B1 | 12/2002 | Rafert |
| 6,511,438 B2 | 1/2003 | Bernstein et al. |
| 6,512,949 B1 | 1/2003 | Combs et al. |
| 6,532,384 B1 | 3/2003 | Fukuda |
| 6,551,252 B2 | 4/2003 | Sackner et al. |
| 6,556,001 B1 | 4/2003 | Wiegand et al. |
| 6,560,480 B1 | 5/2003 | Nachaliel et al. |
| 6,561,986 B2 | 5/2003 | Baura et al. |
| 6,569,160 B1 | 5/2003 | Goldin et al. |
| 6,584,348 B2 | 6/2003 | Glukhovsky |
| 6,602,201 B1 | 8/2003 | Hepp et al. |
| 6,615,077 B1 | 9/2003 | Zhu et al. |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtke |
| 6,633,777 B2 | 10/2003 | Szopinski |
| 6,636,754 B1 | 10/2003 | Baura et al. |
| 6,643,543 B2 | 11/2003 | Takehara et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,725,089 B2 | 4/2004 | Komatsu et al. |
| 6,753,487 B2 | 6/2004 | Fujii et al. |
| 6,760,617 B2 | 7/2004 | Ward et al. |
| 6,768,921 B2 | 7/2004 | Organ et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,845,264 B1 | 1/2005 | Skladnev et al. |
| 6,870,109 B1 | 3/2005 | Villarreal |
| 6,906,533 B1 | 6/2005 | Yoshida |
| 6,922,586 B2 | 7/2005 | Davies |
| 6,980,852 B2 | 12/2005 | Jersey-Willuhn et al. |
| 7,096,061 B2 | 8/2006 | Arad |
| 7,122,012 B2 | 10/2006 | Bouton et al. |
| 7,130,680 B2 | 10/2006 | Kodama et al. |
| 7,148,701 B2 | 12/2006 | Park et al. |
| 7,149,573 B2 | 12/2006 | Wang |
| 7,164,522 B2 | 1/2007 | Kimura et al. |
| 7,169,107 B2 | 1/2007 | Jersey-Willuhn et al. |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,212,852 B2 | 5/2007 | Smith et al. |
| 7,214,107 B2 | 5/2007 | Powell et al. |
| 7,233,823 B2 | 6/2007 | Simond et al. |
| 7,251,524 B1 | 7/2007 | Hepp et al. |
| 7,270,580 B2 | 9/2007 | Bradley et al. |
| 7,353,058 B2 | 4/2008 | Weng et al. |
| 7,390,303 B2 | 6/2008 | Dafni |
| 7,457,660 B2 | 11/2008 | Smith et al. |

(56) References Cited

U.S. PATENT DOCUMENTS

| | | |
|---|---|---|
| 7,477,937 B2 | 1/2009 | Iijima et al. |
| 7,706,872 B2 | 4/2010 | Min et al. |
| 7,733,224 B2 | 6/2010 | Tran |
| 7,749,013 B2 | 7/2010 | Sato et al. |
| 7,907,997 B2 | 3/2011 | Stahmann et al. |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0025139 A1 | 9/2001 | Pearlman |
| 2001/0049479 A1 | 12/2001 | Szopinski |
| 2001/0051774 A1 | 12/2001 | Littrup et al. |
| 2002/0022787 A1 | 2/2002 | Takehara et al. |
| 2002/0072682 A1 | 6/2002 | Hopman et al. |
| 2002/0072686 A1 | 6/2002 | Hoey et al. |
| 2002/0079910 A1 | 6/2002 | Fukuda |
| 2002/0093992 A1 | 7/2002 | Plangger |
| 2002/0123694 A1 | 9/2002 | Organ et al. |
| 2002/0138019 A1 | 9/2002 | Wexler et al. |
| 2002/0161311 A1 | 10/2002 | Ward et al. |
| 2002/0163408 A1 | 11/2002 | Fujii et al. |
| 2002/0194419 A1 | 12/2002 | Rajput et al. |
| 2003/0004403 A1 | 1/2003 | Drinan et al. |
| 2003/0004433 A1 | 1/2003 | Hirschman |
| 2003/0023184 A1 | 1/2003 | Pitts-Crick et al. |
| 2003/0028221 A1 | 2/2003 | Zhu et al. |
| 2003/0050570 A1 | 3/2003 | Kodama |
| 2003/0068914 A1 | 4/2003 | Merry et al. |
| 2003/0073916 A1 | 4/2003 | Yonce |
| 2003/0105411 A1 | 6/2003 | Smallwood |
| 2003/0120170 A1 | 6/2003 | Zhu et al. |
| 2003/0120182 A1 | 6/2003 | Wilkinson et al. |
| 2003/0173976 A1 | 9/2003 | Wiegand et al. |
| 2003/0216664 A1 | 11/2003 | Suarez |
| 2004/0015095 A1 | 1/2004 | Li |
| 2004/0019292 A1 | 1/2004 | Drinan et al. |
| 2004/0054298 A1 | 3/2004 | Masuo et al. |
| 2004/0059242 A1 | 3/2004 | Masuo et al. |
| 2004/0073127 A1 | 4/2004 | Istvan et al. |
| 2004/0073130 A1 | 4/2004 | Bohm et al. |
| 2004/0077944 A1 | 4/2004 | Steinberg et al. |
| 2004/0116819 A1 | 6/2004 | Alt |
| 2004/0158167 A1 | 8/2004 | Smith et al. |
| 2004/0167423 A1 | 8/2004 | Pillon et al. |
| 2004/0171963 A1 | 9/2004 | Takehara |
| 2004/0181164 A1 | 9/2004 | Smith et al. |
| 2004/0186392 A1 | 9/2004 | Ward et al. |
| 2004/0204658 A1 | 10/2004 | Dietz et al. |
| 2004/0210150 A1 | 10/2004 | Virtanen |
| 2004/0210158 A1 | 10/2004 | Organ et al. |
| 2004/0234113 A1 | 11/2004 | Miga |
| 2004/0236202 A1 | 11/2004 | Burton |
| 2004/0242989 A1 | 12/2004 | Zhu et al. |
| 2004/0252870 A1 | 12/2004 | Reeves et al. |
| 2004/0260167 A1 | 12/2004 | Leonhardt et al. |
| 2005/0033281 A1 | 2/2005 | Bowman et al. |
| 2005/0039763 A1 | 2/2005 | Kraemer et al. |
| 2005/0070778 A1 | 3/2005 | Lackey et al. |
| 2005/0080460 A1 | 4/2005 | Wang et al. |
| 2005/0098343 A1 | 5/2005 | Fukuda |
| 2005/0101875 A1 | 5/2005 | Semler et al. |
| 2005/0107719 A1 | 5/2005 | Arad (Abbound) et al. |
| 2005/0113704 A1 | 5/2005 | Lawson et al. |
| 2005/0117196 A1 | 6/2005 | Kimura et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177062 A1 | 8/2005 | Skrabal et al. |
| 2005/0192488 A1 | 9/2005 | Bryenton et al. |
| 2005/0192511 A1 | 9/2005 | Shiokawa |
| 2005/0201598 A1 | 9/2005 | Harel et al. |
| 2005/0203435 A1 | 9/2005 | Nakada |
| 2005/0215918 A1 | 9/2005 | Frantz et al. |
| 2005/0228309 A1 | 10/2005 | Fisher et al. |
| 2005/0261743 A1 | 11/2005 | Kroll |
| 2005/0283091 A1 | 12/2005 | Kink et al. |
| 2006/0004300 A1 | 1/2006 | Kennedy |
| 2006/0041280 A1 | 2/2006 | Stahmann et al. |
| 2006/0064029 A1 | 3/2006 | Arad (Abboud) et al. |
| 2006/0085048 A1 | 4/2006 | Cory et al. |
| 2006/0085049 A1 | 4/2006 | Cory et al. |
| 2006/0110962 A1 | 5/2006 | Powell et al. |
| 2006/0111652 A1 | 5/2006 | McLeod |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0128193 A1 | 6/2006 | Bradley et al. |
| 2006/0135886 A1 | 6/2006 | Lippert et al. |
| 2006/0151815 A1 | 7/2006 | Graovac et al. |
| 2006/0197509 A1 | 9/2006 | Kanamori et al. |
| 2006/0200033 A1 | 9/2006 | Keren et al. |
| 2006/0224079 A1 | 10/2006 | Washchuk |
| 2006/0224080 A1 | 10/2006 | Oku et al. |
| 2006/0241513 A1 | 10/2006 | Hatlestad et al. |
| 2006/0241719 A1 | 10/2006 | Foster et al. |
| 2006/0247543 A1 | 11/2006 | Cornish et al. |
| 2006/0247739 A1 | 11/2006 | Wahlstrand et al. |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0270942 A1 | 11/2006 | McAdams |
| 2006/0293609 A1 | 12/2006 | Stahmann et al. |
| 2007/0007975 A1 | 1/2007 | Hawkins et al. |
| 2007/0010758 A1 | 1/2007 | Matthiessen et al. |
| 2007/0027402 A1 | 2/2007 | Levin et al. |
| 2007/0043303 A1 | 2/2007 | Osypka et al. |
| 2007/0049993 A1 | 3/2007 | Hofmann et al. |
| 2007/0087703 A1 | 4/2007 | Li et al. |
| 2007/0106342 A1 | 5/2007 | Schumann |
| 2007/0156061 A1 | 7/2007 | Hess |
| 2008/0001608 A1 | 1/2008 | Saulnier et al. |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0039700 A1 | 2/2008 | Drinan et al. |
| 2008/0064981 A1 | 3/2008 | Gregory |
| 2008/0205717 A1 | 8/2008 | Reeves et al. |
| 2008/0252304 A1 | 10/2008 | Woo et al. |
| 2008/0270051 A1 | 10/2008 | Essex et al. |
| 2008/0287823 A1 | 11/2008 | Chetham |
| 2008/0319336 A1 | 12/2008 | Ward et al. |
| 2009/0043222 A1 | 2/2009 | Chetham |
| 2009/0054952 A1 | 2/2009 | Glukhovsky et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0082679 A1 | 3/2009 | Chetham |
| 2009/0084674 A1 | 4/2009 | Holzhacker et al. |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0264776 A1 | 10/2009 | Vardy |
| 2009/0287102 A1 | 11/2009 | Ward |
| 2009/0318778 A1 | 12/2009 | Dacso et al. |
| 2010/0100003 A1 | 4/2010 | Chetham et al. |
| 2010/0109739 A1 | 5/2010 | Ironstone et al. |
| 2010/0145164 A1 | 6/2010 | Howell |
| 2010/0168530 A1 | 7/2010 | Chetham et al. |
| 2010/0234701 A1 | 9/2010 | Cho et al. |
| 2011/0060239 A1 | 3/2011 | Gaw |

FOREIGN PATENT DOCUMENTS

| | | |
|---|---|---|
| CA | 2615845 A1 | 1/2007 |
| CN | 1180513 A | 5/1998 |
| CN | 1236597 A | 12/1999 |
| CN | 1329875 A | 1/2002 |
| CN | 1366694 A | 8/2002 |
| CN | 101385203 A | 3/2009 |
| DE | 2912349 A1 | 10/1980 |
| EP | 249823 A1 | 12/1987 |
| EP | 339471 A2 | 11/1989 |
| EP | 349043 A2 | 1/1990 |
| EP | 357309 A2 | 3/1990 |

(56) References Cited

FOREIGN PATENT DOCUMENTS

| | | |
|---|---|---|
| EP | 377887 A1 | 7/1990 |
| EP | 581073 A2 | 2/1994 |
| EP | 662311 A1 | 7/1995 |
| EP | 865763 | 9/1998 |
| EP | 869360 A2 | 10/1998 |
| EP | 1078597 A2 | 2/2001 |
| EP | 1080686 A1 | 3/2001 |
| EP | 1112715 A1 | 7/2001 |
| EP | 1114610 A1 | 7/2001 |
| EP | 1146344 A1 | 10/2001 |
| EP | 1177760 A1 | 2/2002 |
| EP | 1219937 A1 | 7/2002 |
| EP | 1238630 A2 | 9/2002 |
| EP | 1247487 A1 | 10/2002 |
| EP | 1283539 A1 | 2/2003 |
| EP | 1329190 A1 | 7/2003 |
| EP | 1338246 A1 | 8/2003 |
| EP | 1452131 A1 | 9/2004 |
| EP | 1553871 A1 | 7/2005 |
| EP | 1629772 | 3/2006 |
| EP | 1903938 A1 | 4/2008 |
| EP | 1909642 A1 | 4/2008 |
| EP | 1948017 A1 | 7/2008 |
| FR | 2486386 A1 | 1/1982 |
| FR | 2748928 A1 | 11/1997 |
| GB | 2131558 A | 6/1984 |
| GB | 2260416 A | 4/1993 |
| GB | 2426824 | 12/2006 |
| JP | 04-096733 A | 3/1992 |
| JP | 06-000168 A | 1/1994 |
| JP | 8191808 A | 7/1996 |
| JP | 9051884 A | 2/1997 |
| JP | 9220209 A | 8/1997 |
| JP | 10000185 | 1/1998 |
| JP | 10014898 A | 1/1998 |
| JP | 10014899 A | 1/1998 |
| JP | 10-080406 A | 3/1998 |
| JP | 10-225521 A | 8/1998 |
| JP | 11070090 A | 3/1999 |
| JP | 2000107138 A | 4/2000 |
| JP | 2000139867 A | 5/2000 |
| JP | 2001037735 A | 2/2001 |
| JP | 2001-070273 A | 3/2001 |
| JP | 2001061804 A | 3/2001 |
| JP | 2001-224568 A | 8/2001 |
| JP | 2001321352 A | 11/2001 |
| JP | 2002330938 A | 11/2002 |
| JP | 2003116805 A | 4/2003 |
| JP | 2005099186 A | 4/2005 |
| JP | 2005-143786 A | 6/2005 |
| JP | 2008022995 A | 2/2008 |
| NL | 001019789 C2 | 7/2003 |
| RU | 2112416 C1 | 6/1998 |
| RU | 2138193 C1 | 9/1999 |
| SU | 1132911 A1 | 1/1985 |
| WO | 8807392 A1 | 10/1988 |
| WO | 9318821 A1 | 9/1993 |
| WO | 9410922 A1 | 5/1994 |
| WO | 9601586 A1 | 1/1996 |
| WO | 9612439 A1 | 5/1996 |
| WO | 9632652 A1 | 10/1996 |
| WO | 97/11638 | 4/1997 |
| WO | 9714358 A1 | 4/1997 |
| WO | 9743000 A1 | 11/1997 |
| WO | 9806328 A1 | 2/1998 |
| WO | 98/23204 | 6/1998 |
| WO | 98/33553 | 8/1998 |
| WO | 9851211 A1 | 11/1998 |
| WO | 9854792 A1 | 12/1998 |
| WO | 0019886 A1 | 4/2000 |
| WO | 0040955 A1 | 7/2000 |
| WO | 00/79255 | 12/2000 |
| WO | 0127605 A1 | 4/2001 |
| WO | 01/50954 | 7/2001 |
| WO | 01/67098 | 9/2001 |
| WO | 01/78831 A2 | 10/2001 |
| WO | 0182323 A1 | 11/2001 |
| WO | 02/47548 A1 | 6/2002 |
| WO | 02062214 A1 | 8/2002 |
| WO | 02094096 A1 | 11/2002 |
| WO | 02/100267 A1 | 12/2002 |
| WO | 2004000115 A1 | 12/2003 |
| WO | 2004026136 A1 | 4/2004 |
| WO | 2004030535 A1 | 4/2004 |
| WO | 2004032738 A1 | 4/2004 |
| WO | 2004/047636 | 6/2004 |
| WO | 2004/048983 | 6/2004 |
| WO | 2004047635 A1 | 6/2004 |
| WO | 2004047638 A1 | 6/2004 |
| WO | 2004049936 A2 | 6/2004 |
| WO | 2004083804 A2 | 9/2004 |
| WO | 2004/084723 | 10/2004 |
| WO | 2004/084724 | 10/2004 |
| WO | 2005010640 A2 | 2/2005 |
| WO | 2005018432 A2 | 3/2005 |
| WO | 2005027717 A2 | 3/2005 |
| WO | 2005/051194 | 6/2005 |
| WO | 2005/084539 | 9/2005 |
| WO | 2005/122888 | 12/2005 |
| WO | 2005122881 A1 | 12/2005 |
| WO | 2006/129108 | 12/2006 |
| WO | 2006129116 A1 | 12/2006 |
| WO | 2007/002993 | 1/2007 |
| WO | 2007002991 A1 | 1/2007 |
| WO | 2007002992 A1 | 1/2007 |
| WO | 2007009183 A1 | 1/2007 |
| WO | 2007014417 A1 | 2/2007 |
| WO | 2007/041783 | 4/2007 |
| WO | 2007089278 A1 | 8/2007 |
| WO | 2008064426 A1 | 6/2008 |
| WO | 2008/119166 | 10/2008 |
| WO | 2008138062 A1 | 11/2008 |
| WO | 2009036369 A1 | 3/2009 |
| WO | 2009/059351 | 5/2009 |
| WO | 2009/100491 | 8/2009 |
| WO | 2010/051600 | 5/2010 |
| WO | 2010/060152 | 6/2010 |
| WO | 2011022068 A1 | 2/2011 |
| WO | 2011050393 A1 | 5/2011 |
| WO | 2011075769 A1 | 6/2011 |

OTHER PUBLICATIONS

Gudivaka et al., Single- and multifrequency models for bioelectrical impedance analysis of body water compartments, Appl. Physiol., 1999; 87(3), 1087-96.
U.S. Appl. No. 13/128,631, Essex et al.
U.S. Appl. No. 13/131,859, Gaw.
U.S. Appl. No. 12/090,078, filed Feb. 12, 2009, Chetham.
U.S. Appl. No. 12/516,876, filed Jul. 1, 2010, Chetham.
U.S. Appl. No. 12/596,833, filed Jun. 17, 2010, Ward.
U.S. Appl. No. 12/600,224, Chetham.
U.S. Appl. No. 12/672,893, filed Feb. 24, 2011, Cornish.
U.S. Appl. No. 10/767,825, filed Sep. 23, 2004, Ward.
d'Entremont et al. "Impedance spectroscopy: an accurate method of differentiating between viable and ischaemic or infarcted muscle tissue" Med. Biol. Eng. Comput., 2002, 40: 380-87.
Zhu et al., "Dynamics of segmental extracellular volumes during changes in body position by bioimpedance analysis"; J. App. Physiol.; 1998, vol. 85, pp. 497-504.
McCullagh, W. A., et al., Bioelectrical impedance analysis measures the ejection fraction of the calf muscle pump, IFMBE Proceedings, 2007; vol. 17, p. 619.
European Search Report for EP 07718972.8-1265 / 2020918 (Impedimed, Ltd.), mailed on Mar. 2, 2010, 4 pages.
Brown et al.; Relation between tissue structure and imposed electrical current flow in cervical neoplasis; The Lancet; Mar. 11, 2000; vol. 355, Issue 9207: pp. 892-895.
Ellis et al.; Human hydrometry: comparison of multifrequency bioelectrical impedance with 2H2O and bromine dilution; Journal of Applied Physiology; 1998; 85(3): 1056-1062.

(56) References Cited

OTHER PUBLICATIONS

Jones et al.; Extracellular fluid volume determined by bioelectric impedance and serum albumin in CAPD patients; Nephrology Dialysis Transplantation; 1998; 13: 393-397.

Thomas B.J.; Future technologies; Asia Pacific Journal Clinical Nutrition; 1995; 4: 157-159.

Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; Oct. 31, 1996; 5: 1934-1935.

Woodrow et al.; Effects of icodextrin in automated peritoneal dialysis on blood pressure and bioelectrical impedance analysis; Nephrology Dialysis Transplantation; 2000; 15: 862-866.

Boulier et al.; Fat-Free Mass Estimation by Two Electrode Impedance Method; American Journal of Clinical Nutrition; 1990; 52: 581-585.

McDougal et al.; Body Composition Measurements from Whole Body Resistance and Reactance; Surgical Forum; 1986; 36: 43-44.

Tedner, B.; Equipment using Impedance Technique for Automatic Recording of Fluid-Volume Changes during Hemodialysis; Medical & Biological Engineering & Computing; 1983; 285-290.

Lukaski et al.; Estimation of Body Fluid Volumes using Tetrapolar Bioelectrical Impedance Measurements; Aviation, Space, and Environmental Medicine; Dec. 1988; 1163-1169.

Lozano et al.; Two-frequency impedance plethysmograph: real and imaginary parts; Medical & Biological Engineering & Computing; Jan. 1990; 28(1): 38-42.

Chaudary et al.; Dielectric Properties of Normal & Malignant Human Breast Tissues at Radiowave and Microwave Frequencies; Indian Journal of Biochemistry & Biophysics; 1984; 21(1): 76-79.

Jossinet et al.; A study for breast imaging with a circular array of impedance electrodes; Proc. Vth Int. Conf. Bioelectrical Impedance, 1981, Tokyo, Japan; 1981; 83-86.

Jossinet et al.; Technical Implementation and Evaluation of a Bioelectrical Breast Scanner; Proc. 10.supth Int. Conf. IEEE Engng. Med. Biol., 1988, New Orleans, USA (Imped. Imaging II); 1988; 1: 289.

Man et al.; Results of Preclinical Tests for Breast Cancer Detection by Dielectric Measurements; XII Int. Conf. Med. Biol. Engng. 1979, Jerusalem, Israel. Springer Int., Berlin; 1980; Section 30.4.

Pethig et al.; The Passive Electrical Properties of Biological Systems: Their Significance in Physiology, Biophysics and Biotechnology; Physics in Medicine and Biology; 1987; 32: 933-970.

Piperno et al.; Breast Cancer Screening by Impedance Measurements; Frontiers of Medical & Biological Engineering; 1990; 2: 111-117.

Skidmore et al.; A Data Collection System for Gathering Electrical Impedance Measurements from the Human Breast; Clinical Physics Physiological Measurement; 1987; 8: 99-102.

Sollish et al.; Microprocessor-assisted Screening Techniques; Israel Journal of Medical Sciences; 1981; 17: 859-864.

Surowiec et al.; Dielectric Properties of Breast Carcinima and the Surrounding Tissues; IEEE Transactions on Biomedical Engineering; 1988; 35: 257-263.

Al-Hatib, F.; Patient Instrument Connection Errors in Bioelectrical Impedance Measurement; Physiological Measurement; May 2, 1998; 19(2): 285-296.

Gersing, E.; Impedance Spectroscopy on Living Tissue for Determination of the State of Organs; Bioelectrochemistry and Bioenergetics; 1998; 45: 145-149.

Mattar, J.A.; Application of Total Body Impedance to the Critically Ill Patient; New Horizons; 1996; 4(4): 493-503.

Ott et al.; Bioelectrical Impedance Analysis as a Predictor of Survival in Patients with Human Immunodeficiency Virus Infection; Journal of Acquired Immune Deficiency Syndromes and Human Retrovirology; 1995; 9: 20-25.

Thomas et al.; Bioelectrical impedance analysis for measurement of body fluid volumes—a review; Journal of Clinical Engineering; 1992; 17(16): 505-510.

Ward et al.; There is a better way to measure Lymphedema; National Lymphedema Network Newsletter; Oct. 1995; 7(4): 89-92.

Cornish et al.; Alteration of the extracellular and total body water volumes measured by multiple frequency bioelectrical impedance analysis; Nutrition Research; 1994; 14(5): 717-727.

Cornish et al.; Early diagnosis of lymphedema using multiple frequency bioimpedance; Lymphology; Mar. 2001; 34: 2-11.

Cornish et al.; Early diagnosis of lymphoedema in postsurgery breast cancer patients; Annals New York Academy of Sciences; May 2000; 571-575.

Brown et al.; Relation between tissue structure and imposed electrical current flow in cervical neoplasia; The Lancet; Mar. 11, 2000; 355 (9207): 892-895.

Iacobellis, G. et al.; Influence of excess fat on cardiac morphology and function: Study in Uncomplicated obesity; Obesity Research; Aug. 8, 2002; 10 (8): 767-773.

Bella, J. N. et al.; Relations of left ventricular mass to fat-free and adipose body mass: The Strong Heart Study; Circulation; Dec. 12, 1998; 98: 2538-2544.

Yoshinaga, M. et al.; Effect of total adipose weight and systemic hypertension on left ventricular mass in children; American Journal of Cardiology; Oct. 15, 1995; 76: 785-787.

Karason, K. et al.; Impact of blood pressure and insulin on the relationship between body fat and left ventricular structure; European Heart Journal; Jan. 1, 2003; 24: 1500-1505.

Abdullah M. Z.; Simulation of an inverse problem in electrical impedance tomography using resistance electrical network analogues; International Journal of Electrical Engineering Education; Oct. 1999; 36 (4): 311-324.

Dines et al.; Analysis of electrical conductivity imaging; Geophysics; Jul. 1981; 46 (7): 1025-1036.

Osterman et al.; Multifrequency electrical impedance imaging: preliminary in vivo experience in breast; Physiological Measurement; Feb. 2000; 21 (1): 99-109.

Ward et al.; Determination of Cole parameters in multiple frequency bioelectrical impedance analysis using only the measurement of impedances; Four-frequency fitting; Physiological Measurement; Sep. 2006; 27 (9): 839-850.

Bernstein; A new stroke volume equation for thoracic electrical bio impedance; Critical Care Medicine; 1986; vol. 14; pp. 904-909.

McAdams et al.; Tissue Impedance: a historical overview; Physiological Measurement, Institute of Physics Publishing, Bristol, GB; 16 (3A); pp. A1-A13; Aug. 1, 1995.

Forslund et al., Evaluation of modified multicompartment models to calculate body composition in healthy males, Am. J. of Clin. Nutrition, 1996; 63:856-62.

Van Loan et al., Use of bioelectrical impedance spectroscopy (BIS) to measure fluid changes during pregnancy, J. Appl. Physiol., 1995; 78:1037-42.

De Lorenzo et al., Predicting body cell mass with bioimpedance by using theoretical methods: a technological review, J. Appl. Physiol., 1997; 82(5):1542-58.

Zhu et al., Segment-specific resistivity improves body fluid volume estimates from bioimpedance spectroscopy in hemodialysis patients, J. Appl. Physiol., Oct. 27, 2005; 100:717-24.

Thomas et al., Bioimpedance Spectrometry in the Determination of Body Water Compartments: Accuracy and Clinical Significance, Applied Radiation and Isotopes, 1998; 49(5/6):447-455, Elsevier Science Ltd., Oxford, GB.

Cornish et al., Data analysis in multiple-frequency bioelectrical impedance analysis, Physiological Measurement, 1998; 19(2):275-283, Institute of Physics Publishing, Bristol, GB.

Ulgen et al., Electrical Parameters of Human Blood, Proc. of the 20th Annual Int'l Conference of the IEEE Engineering in Medicine and Biology Soc., 1998; 20(6):2983-2986, IEEE Piscataway, NJ.

Bracco et al., Bedside determination of fluid accumulation after cardiac surgery usign segmental bioelectrical impedance, 1998, Critical Care Medicine, vol. 26 No. 6, pp. 1065-1070.

Chiolero et al., Assessmetn of changes in body water by bioimpedance in acutely ill surgical patients, 1992, Intensive Care Medicine, vol. 18, pp. 322-326.

(56) References Cited

OTHER PUBLICATIONS

Chumlea et al., Bioelectrical impedance and body composition: present status and future directions, 1994 Nutrition Reviews, vol. 52, No. 4, pp. 123-131.

Cornish et al., Bioelectrical impedance for monitoring the efficacy of lymphoedema treatment programmes, 1996, Breast Cancer Research and Treatment, vol. 38, pp. 169-176.

Cornish et al., Quantification of lymphoedema using multi-frequency bioimpedance, 1998, Applied Radiation and Isotopes, vol. 49 No. 5/6, pp. 651-652.

De Luca et al., Use of low-frequency electrical impedance mesurements to determine phospholipid content in amniotic fluid, 1996, Physics in Medicine and Biology, vol. 41, pp. 1863-1869.

Derwent Abstract No. 97-474414, JP 09 220209 A (Sekisui Chem Ind Co Ltd) Aug. 26, 1997, see abstract.

Derwent Abstract No. 99-138541, JP 10 014898 A (Sekisui Chem Ind Co Ltd) Jan. 20, 1998, see abstract.

Derwent Abstract No. 99-138542, JP 10 014899 A (Sekisui Chem Ind Co Ltd) Feb. 20, 1998, see abstract.

Derwent Abstract No. 99-247542, JP 11 070090 A (Sekisui Chem Ind Co Ltd) Mar. 16, 1999, see abstract.

Duerenberg et al., Multi-frequency bioelectrical impedance: a comparison between the Cole-Cole modelling and Hanai equations with the classical impedance index approach, 1996, Annals of Human Biology, vol. 23, No. 1, pp. 31-40.

Kim et al., Bioelectrical impedance changes in regional extracellular fluid alterations, 1997, Electromyography and Clinical Neurophysiology, vol. 37, pp. 297-304.

Rigaud et al., Biolectrical impedance techniques in medicine, 1996, Critical Reviews in Biomedical Engineering, vol. 24 (4-6), pp. 257-351.

Steijaert et al., The use of multi-frequency impedance to determine total body water and extracellular water in obese and lean female individuals, 1997, International Journal of Obesity, vol. 21, pp. 930-934.

Ward et al., Multi-frequency bioelectrical impedance augments the diagnosis and management of lymphoedema in post-mastectomy, 1992, European Journal of Clinical Investigation, vol. 22, pp. 751-754.

Gerth et al., A Computer-based Bioelectrical Impedance Spectroscopic System for Noninvasive Assessment of Compartmental Fluid Redistribution, Third Annual IEEE Symposium on Computer-Based Medical Systems Track 6: Clinical Assessment and Risk Evaluation/Session 13, 1990; 446-453.

Kanai et al., Electrical measurement of fluid distribution in legs and arms, Dept. of Electrical Engineering, Sophia University, 1987; Medical Progress through Technology 12: 159-170, Copyright Martinus Nijhoff Publishers, Boston, MA USA.

IMPEDANCE MEASUREMENTS

CROSS-REFERENCE TO RELATED APPLICATIONS

This application is a §371 national phase of International application PCT/AU2007/000726 filed May 25, 2007, which claims foreign priority to Australian Patent Application no. 2006-902907 filed May 30, 2006.

BACKGROUND OF THE INVENTION

The present invention relates to a method and apparatus for determining frequencies for use in performing impedance measurements on a subject, as well as to a method and apparatus for performing impedance measurements.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Bioelectrical Impedance Analysis (BIA) measures the impedance to flow of an alternating electrical current passed through biological tissue. Such impedance measurements are typically performed at a number of different frequencies, allowing a subject's impedance response to be modelled, using a mathematic relationship, such as the Cole model. This in turn enables the estimation of various parameters, which can in turn be used to derive information regarding a subject's health.

However, the frequencies used are typically selected randomly, or based on the ability of the measuring device used to perform the measurements. Consequently the effectiveness and accuracy of the measurements varies greatly.

SUMMARY OF THE PRESENT INVENTION

In a first broad form the present invention provides a method of determining frequencies for use in performing impedance measurements, the method including:
 a) determining estimates for parameter values representing an impedance response for at least one subject;
 b) using the estimated parameter values to determine a design; and,
 c) using the design to determine frequencies for use in impedance measurements.

Typically the method includes, determining the estimates for the parameter values at least in part using a model of the subject's impedance response.

Typically the method includes:
 a) determining a residual variance model having a predetermined distribution; and,
 b) determining the estimates for the parameter values at least in part using the selecting variance model.

Typically the method of determining the residual variance model includes using an expectation maximization algorithm.

Typically the method includes determining a range of parameter values representing the impedance response of a number of subjects.

Typically the method includes:
 a) determining a Fisher information matrix for a model of the impedance response of the at least one subject; and,
 b) determining a design using the Fisher information matrix.

Typically the model includes at least one of:
 a) A Cole model; and,
 b) A residual variance model.

Typically the model includes determining the design by optimising the determinant of the Fisher information matrix.

Typically the design is a D-optimal design.

Typically the method includes determining a design space to take into account practical limitations.

Typically the method includes, modifying the design by at least one of:
 a) restricting the frequencies; and,
 b) providing an error structure as a function of frequency.

Typically the method is performed at least in part using a processing system.

Typically the method includes, in the processing system:
 a) determining impedance data representing the impedance response of the at least one subject; and,
 b) using the impedance data to determine the estimates for the parameter values.

Typically the method includes, in the processing system:
 a) determining an impedance model; and,
 b) using the impedance model and the estimated parameter values to determine the design.

Typically the method includes, in the processing system:
 a) calculating a Fisher information matrix for the model; and,
 b) using the Fisher information matrix to determine the design.

Typically the method includes, in the processing system, optimising a determinant of the Fisher information matrix for the model.

Typically the method includes, in the processing system:
 a) receiving limits on applicable frequencies; and,
 b) using the limits and the design to determine the frequencies.

Typically the method includes, in the processing system, determining frequencies for use in impedance measurements within the range:
 a) 0-50 kHz;
 b) 2-200 kHz;
 c) 50-500 kHz; and,
 d) 200-1000 kHz.

Typically the frequencies are within the ranges:
 a) 0-24 kHz;
 b) 5-74 kHz;
 c) 77-200 kHz;
 d) 530-1000 kHz.

Typically the frequencies are:
 a) 14 kHz
 b) 57 kHz
 c) 188 kHz
 d) 679 kHz

Typically the frequencies are:
 a) 14.1844 kHz
 b) 56.9201 kHz
 c) 187.5397 kHz
 d) 679.1141 kHz In a second broad form the present invention provides apparatus for determining frequencies for use in performing impedance measurements, the apparatus including, a processing system for:

a) determining estimates for parameter values representing an impedance response for at least one subject;
b) using the estimated parameter values to determine a design; and,
c) using the design to determine frequencies for use in impedance measurements.

Typically the apparatus is for performing the first broad form of the invention.

In a third broad form the present invention provides a method of measuring the impedance of a subject the method including, the method including, in a measuring device:
a) causing one or more electrical signals to be applied to the subject using a first set of electrodes, the one or more electrical signals having four frequencies;
b) measuring electrical signals across a second set of electrodes applied to the subject in response to the applied one or more signals;
c) determining from the applied signals and the measured signals at least one measured impedance value at each of the four frequencies, wherein the four frequencies are in the ranges:
i) 0-50 kHz;
ii) 2-200 kHz;
iii) 50-500 kHz; and,
iv) 200-1000 kHz.

Typically a restricted range of frequencies can be defined by the ranges:
a) 0-24 kHz;
b) 5-74 kHz;
c) 77-200 kHz;
d) 530-1000 kHz.

Typically the frequencies are approximately:
a) 14 kHz
b) 57 kHz
c) 188 kHz
d) 679 kHz Typically the frequencies are:
a) 14.1844 kHz
b) 56.9201 kHz
c) 187.5397 kHz
d) 679.1141 kHz Typically the method includes determining one or more impedance parameter values based on the plurality of measured impedance values.

In a fourth broad form the present invention provides apparatus for measuring the impedance of a subject the apparatus including a measuring device for:
a) causing one or more electrical signals to be applied to the subject using a first set of electrodes, the one or more electrical signals having four frequencies;
b) measuring electrical signals across a second set of electrodes applied to the subject in response to the applied one or more signals;
c) determining from the applied signals and the measured signals at least one measured impedance value at each of the four frequencies, wherein the four frequencies are in the ranges:
i) 0-50 kHz;
ii) 2-200 kHz;
iii) 50-500 kHz; and,
iv) 200-1000 kHz.

Typically the measuring device includes:
a) a current source for applying current signals to the subject;
b) a voltage sensor for measuring voltages signals across the subject; and,
c) a processing system could to the current source and the voltage sensor for:
i) causing the current signals to be applied to the subject; and,
ii) determining the impedance using the applied current signals and measured voltage signals.

Typically the apparatus is for performing the method of the third broad form of the invention.

BRIEF DESCRIPTION OF THE DRAWINGS

Examples of the present invention will now be described with reference to the accompanying drawings, in which:—

DETAILED DESCRIPTION OF THE PREFERRED EMBODIMENTS

Figure 1:
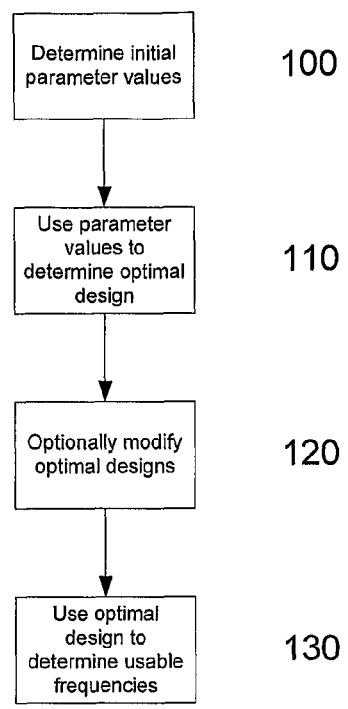
FIG. 1 is a flow chart of an example of a process for determining frequencies for use in performing impedance measurements.

An example of a process for determining frequencies at which impedance measurements may be made will now be described with reference to FIG. 1.

At step 100 parameter values are determined representing the impedance response of one or more subjects. The parameter values may be determined in any one of a number of manners, such by modelling impedance data collected from a number of subjects from a prior study, as will be described in more detail below.

At step 110 the parameter values are used to determine an optimal design for studying the impedance response of the one or more subjects. This can be achieved, for example, by optimising designs representing frequencies that may be used in performing impedance measurements according to optimality criteria.

At step 120 the optimal designs may optionally be modified to take into account practical effects, such as the variants of subjects within a population to impedance measurement.

At step 130 the optimal designs are used to determine frequencies that may be used for performing impedance measurements.

The process may be performed manually, but typically requires advanced computation and therefore typically requires the use of a processing system.

Figure 2:
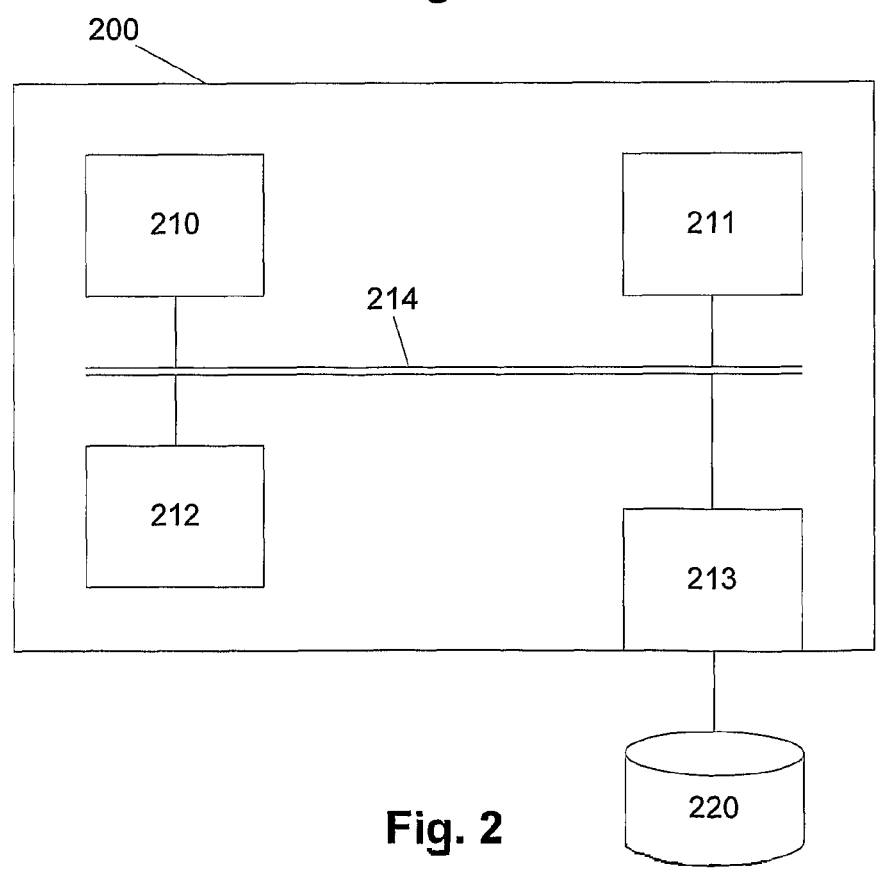
FIG. 2 is a schematic diagram of an example of a processing system for use in determining frequencies.

An example processing system is shown in FIG. 2. In this example, the processing system 200 is formed from a processor 210, a memory 211, an input/output device 212 and an optional external interface 213 interconnected via a bus 214. The external interface 213 may be used to couple the processing system 200 to a database 220.

In use the processing system 200 executes applications software stored in the memory 211, to allow parts of the process to be performed, as will be described in more detail below. It will be appreciated from this that the processing system 200 may be any suitable form of processing system 200, such as a personal computer, desktop, laptop, super computer, Sparc station, or the like.

Figure 3:
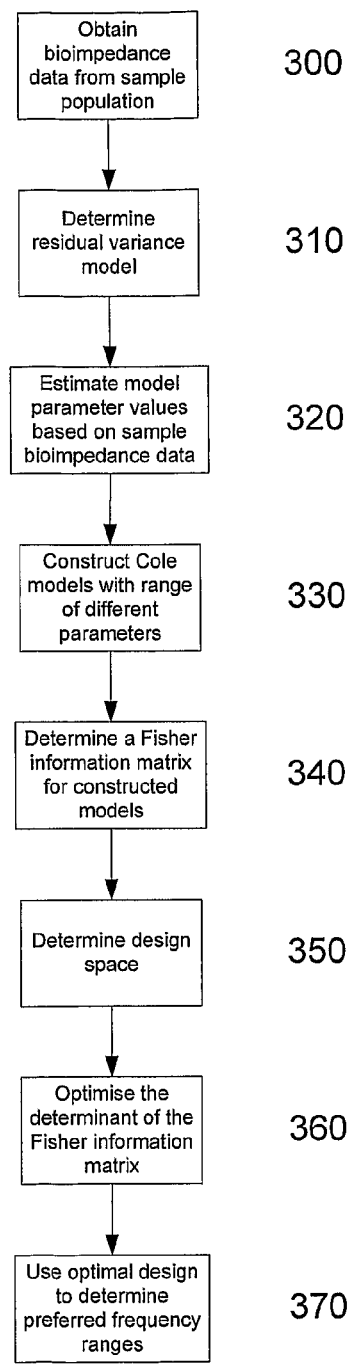
FIG. 3 is a flow chart of a specific example of a process for determining frequencies for use in performing impedance measurements.

An example of the process will now be described in more detail with respect to FIG. 3.

In this example, at step 300 impedance data is collected from a sample population of subjects. The data is collected using a suitable measuring device that applies alternating electrical signals to a subject, and measures the electrical response of the subject. This is typically achieved by applying alternating currents to the subject at a number of different frequencies, and then measures voltage signals across the subject, to allow the impedance to be determined at each frequency. An example measuring device will be described in more detail below.

Figure 4:
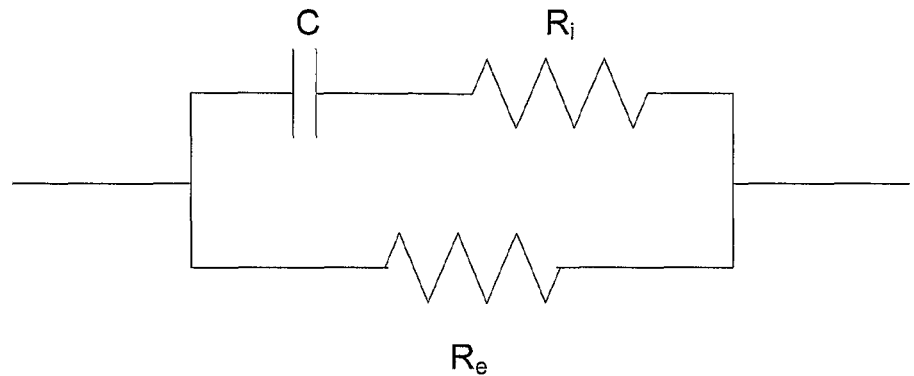
FIG. 4 is a schematic diagram of an example of an "idealised" equivalent circuit for the Cole model.

The impedance response of the subject can be modelled using a suitable model, such the Cole model, which is based on an equivalent circuit that effectively models the electrical behaviour of biological tissue, an example of which is shown in FIG. 4.

In this example, the equivalent circuit includes two branches representing current flow through extracellular fluid and intracellular fluid. The extracellular component of biological impedance is represented by a resistance $R_e$, whilst the intracellular component is represented by a resistance $R_i$ and a capacitance C.

Accordingly, the impedance of the equivalent circuit of FIG. 4 at an angular frequency ω, where ω=2π*frequency, is given by:

$$Z = R_\infty + \frac{R_0 - R_\infty}{1 + (j\omega\tau)} \quad (A)$$

where:
$R_\infty$=impedance at infinite applied frequency=$R_i R_e/(R_i+R_e)$,
$R_0$=impedance at zero applied frequency=$R_e$ and,
τ is the time constant of the capacitive circuit.

However, as an alternative to the equivalent circuit described above, an alternative equivalent circuit incorporating a Fricke constant phase element (CPE) can be used, as will be understood by persons skilled in the art.

In any event, the equation (A) can be modified to include an exponent α to account for the distribution of time constants observed in biological tissues (or systems), as follows:

$$Z = R_\infty + \frac{R_0 - R_\infty}{1 + (j\omega\tau)^{1-\alpha}} \quad (B)$$

In this equation, $R_1$, $R_e$, C and α are parameters in the model, Z is the predicted impedance, $j=\sqrt{-1}$ and f is the frequency of the current passed through the body. $R_1$ and $R_e$ are the resistances due to the intracellular and extracellular fluids in the body, respectively.

However, this is a theoretical model and in practice a subject's response will vary. Accordingly, at step 310 a residual variance model is selected to allow variations from the predicted response to be taken into account. The residual variance model may be selected in any one of ways as will be described in more detail below.

At step 320, parameter estimates are determined that represent the measured responses of the subjects. The initial parameters are parameters which when inserted into the models provide an estimate of the response of the sample population.

It will be appreciated that as different subjects within the sample population will have a range of different responses to impedance measurements. Accordingly, it is typical to model the range of responses across the sample population to allow the mean and variability of the parameters between subjects to be determined. This is effectively used to define a range of parameter values representing a parameter space.

At step 330, a number of Cole models are constructed across the parameter space, using the range of parameter values. This effectively models the range of different impedance responses of the subjects within the population.

At step 340 a Fisher information matrix is determined for the residual and Cole models. This can be achieved in any one of a number of ways, but typically involves using suitable applications software, such as the software package POPT by S. B. Duffull, implemented by the processing system 200.

At step 350, the product determinant of the Fisher information matrices is optimised. Again, this may be achieved in any one of a number of manners, such as by using a simulated annealing approach to find maxima for the expression. This provides an optimised design which represents the theoretical preferred frequencies at which impedance measurements may be made.

However, certain frequency measurements may not be practically achievable, or desirable. Thus, for example, theory may predict that the application of an electrical signal 0 kHz frequency will result in an improved subject response and hence improved impedance measurements. However, as the application of such a frequency is not practical, such a frequency is usually excluded. Similarly, high frequency measurements whilst theoretically advantageous, can be difficult to measure from a practical point of view, thereby further limiting the range of available frequencies. Accordingly, at step 360, a design space is selected that can be used to exclude such impractical frequencies.

At step 370 the optimal design can be used to determine preferred practical frequencies at which impedance measurements may be performed, together with an indication of the relative efficiency of the measurement procedure.

Accordingly, the above-described process operates by utilising impedance measurements for a sample population to determine optimal design, which can in turn be used to determine preferred frequencies for performing impedance measurements.

In one example, described in more detail in the specific example below, the process is used to determine that in general at least four frequencies should be used for performing impedance measurements. This can also be used to determine preferred frequency ranges for the four frequencies.

In one example, the preferred frequency ranges are as follows:
0-50 kHz;
2-200 kHz;
50-500 kHz; and,
200-1000 kHz.

Limiting the design space based on practical constraints can lead to more specific frequency ranges as follows:
0-24 kHz;
5-74 kHz;
77-200 kHz;
530-1000 kHz.

Even more preferably, the range of frequencies can be further limited to specific values as follows:

14 kHz 57 kHz 188 kHz 679 kHz

These are based on theoretical preferred frequencies calculated to be as follows:

14.1844 kHz 56.9201 kHz 187.5397 kHz 679.1141 kHz

Figure 5:
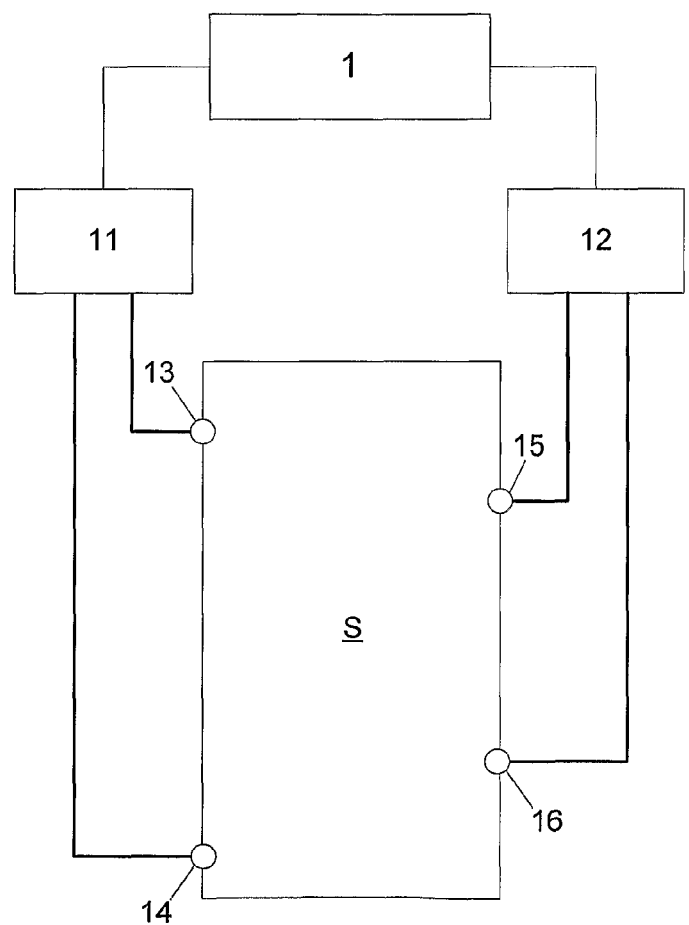
FIG. 5 is a schematic diagram of an example of apparatus for measuring impedance.

Determination of the frequencies allows an impedance measuring device to be provided, which is adapted to utilise the preferred frequencies, as shown for example in FIG. 5.

In this example the impedance measuring device typically includes a processing system 1 coupled to a current source 11 and a voltage sensor 12. The current source 11 is coupled via electrodes 13, 14 to a subject S with the voltage sensor being coupled to the subject S via electrodes 15, 16.

In use the processing system 1 causes the current source 11 to apply alternating current signals to the subject S via the electrodes 13, 14, at each of the preferred frequencies determined using the above described process. The response of subject S is then measured via the electrodes 15, 16 using the voltage sensor 12. The processing system 1 can then use details of the applied current and the measured voltage signals to determine an impedance value at each of the preferred frequencies.

By utilising the four measured frequencies, this allows parameters of the Cole model to be determined, such as the subject's impedance at a characteristic frequency $Z_c$, as well as values for the intracellular and extracellular impedance. This in turn allows information such as indicators of the subject's of intracellular or extracellular fluid, or the ratio there between, to be determined.

Specific Example

A specific example of the above process will now be described in more detail.

In this example, the Cole equation described in Cole, K S (1940) Permeability and impermeability of cell membranes for ions Cold Spring Harbor Symposia on Quantitative Biology 8 110-122, is used to model bioimpedance. The model includes nonlinear parameters, which are known to vary between individuals. Accordingly the process uses the theory of experimental design to find the frequencies at which measurements of bioimpedance are optimally made. This can also be used to determine how many frequencies are needed in each patient in order to obtain good estimates of the parameters.

Experimental Design

Much of experimental design focuses on parameter estimation. A design is optimized, that is, the best choice of covariate settings and experimental effort is chosen, through assessment of an optimality criterion. Criteria considered in this paper are D-optimality and product design optimality, which are typically used to gain good parameter estimates for one or more models. Such criteria are based on the expected Fisher information matrix described in more detail below.

A Design $\xi$ is defined by:

$$\xi = \begin{Bmatrix} x_1 & w_1 \\ x_2 & w_2 \\ \vdots & \vdots \\ x_n & w_n \end{Bmatrix}$$

where $w_i$ is the experimental effort given to the i-th vector of covariates $x_i$.

Use of the experimental effort factor is optional and included in this design for the purpose of example only and the following discussion will focus in examples in which the experimental effort is not taken into account, in which case the preferred Design $\xi$ is defined by:

$$\xi = \begin{Bmatrix} x_1 \\ x_2 \\ \vdots \\ x_n \end{Bmatrix}$$

If $x_i \in \chi$, then the design space can be written as $$\Xi = \left\{ \xi \varepsilon \chi^n \times [0, 1]^n : \sum_{i=1}^{n} \omega_i = 1 \right\}.$$

Fisher Information Matrix

For a model with response vector $y=(y_1,\ldots,y_n)$, dependent upon parameters $\theta$ and a design $\xi$, the expected Fisher information matrix can be defined as:

$$M(\theta, \xi) = -E\left[\frac{\partial^2 l(\theta; y)}{\partial \theta \partial \theta'}\right] \quad (1)$$

where $l(\theta; y)$ is the log-likelihood.

The Cramer-Rao lower bound described in H. Cramer "Mathematical methods of statistics." *Princeton, N.J.: Princeton University Press*, pages 474-477, 1946, states that the variance-covariance matrix of any unbiased estimator of $\theta$ is bounded below by $M^{-1}(\theta,\xi)$. Thus, for given a design $\xi$, the expected Fisher information indicates how well to estimate the parameters in the model.

D-Optimality

A design $\xi$ is D-optimal if it maximizes the determinant of the expected fisher information matrix. That is, arg max$_\xi$|M($\theta,\xi$)|. This design will minimize |M$^{-1}(\theta,\xi)$| which, minimizes the variance-covariance of $\hat{\theta}$. Such D-optimal designs, therefore, in general provide good estimates of parameters since they minimise the ellipsoidal confidence regions around an estimate.

When comparing a designs ability to estimate model parameters, its D-efficiency is considered. The D-efficiency of the design $\xi$ compared to the D-optimal design $\xi^*$ for a particular model is:

$$Deff = \left\{ \frac{|M(\xi, \theta)|^{1/p_1}}{|M(\xi^*, \theta)|^{1/p_1}} \right\} \quad (2)$$

where $p_i$ is the number of parameters in the model.

A D-efficiency of 0.5 for $\xi$ compared with $\xi^*$ means that twice as many samples need to be taken using $\xi$ in order to obtain as accurate parameter estimates as given by $\xi^*$.

Product Design Optimality

Product design is found when trying to obtain efficient parameter estimates for more than one model. Here the product of the determinants, scaled by the number of parameters, of each model is maximized giving a design $\xi^*_{D_1,D_2}$ which should yield good parameter estimates under each model. That is, $$\xi^*_{D_1,D_2} = \arg\max_{\xi}\{|M_1(\theta^1,\xi)|^{1/p_1}|M_2(\theta^2,\xi)|^{1/p_2}\} \quad (3)$$

where $M_1(\theta_1,\xi)$ is the expected Fisher information matrix for model 1 with parameters $\theta_1$ and $p_1$ is the number of model parameters. Similarly for model 2.

Nonlinear Regression

A nonlinear model is specified by two main parts; a function expressing the predicted response and residual response variance structure. This, for the jth observation, can be written as follows:

$$y_j = f(x_j,\theta) + \epsilon_j \quad (4)$$

where:
- $y_j$ is the jth predicted response,
- $x_j$ are the covariates,
- $\theta$ refers to the model parameters and
- $\epsilon_j$ is error or uncertainty in the response for a given individual.

When modelling nonlinear data it is assumed that:

(i) $E[\epsilon_j]=0$; for $j=1,\ldots,m$
(ii) $Cor[\epsilon_j,\epsilon_l]=0$; for $j=1,\ldots,m$ and for $l=1,\ldots,m$
(iii) $Var[\epsilon_j]=\sigma^2$, and are identically distributed for all $x_j$ for $j=1,\ldots,m$;
(iv) $\epsilon_j \sim N(\mu,\sigma^2)$ for $j=1,\ldots,m$.

Often in practical applications, some of these assumptions do not hold. Accordingly, some generalizations or relaxations of this framework can be used so that the theory of nonlinear regression can be applied in these areas.

One relaxation is a generalization of the assumption of constant variance. Such a relaxation will allow flexibility in specifying intra-individual variance. This involves specifying a variance function h which can depend upon the predicted response $E[y_j]$, covariates $x_j$ and/or additional parameters $\delta$. The model is then specified by:

$$E[y_j] = f(x_j,\theta)$$

$$Var[y_j] = \sigma^2 h^2(\mu_j,x_j,\delta)$$

$$\mu_j = f(x_j,\theta)$$

Such a specification generalizes assumption (iii) and allows for heteroscedasticity in the model.

The above defines a fixed effects model. However, to take into account variations between individuals, mixed effects models are typically used.

Fixed Effects Models

For a single individual, a fixed effects model (of the form $y_i=f(x_i,\theta)+\epsilon_i$) is considered. The expected fisher information matrix is defined as follows:

$$-E\left[\frac{\partial^2 l(\theta;y)}{\partial\theta\partial\theta'}\right] = JWJ' \quad (5)$$

where:

$$J = \begin{bmatrix} \frac{\partial f(\theta,\xi)}{\partial\theta_1} \\ \frac{\partial f(\theta,\xi)}{\partial\theta_2} \\ \vdots \\ \frac{\partial f(\theta,\xi)}{\partial\theta_n} \end{bmatrix}$$

and W is a diagonalized n×1 vector of weights and $$\frac{\partial f(\theta,\xi)}{\partial\theta_i}$$

is a row vector of derivatives of the model with respect to the ith parameter evaluated at the covariates in $\xi$.

Mixed Effects Models

Mixed effects models allow for the analysis of individual data by incorporating fixed and random effects into a model. This gives two sources of variation; residuals within individuals and variation between individuals. Accordingly, the models have two types of coefficients; population-average and individual specific. One of the main applications of this theory is to repeated measures data.

It is known that where $y_i$ is a $n_i$-vector of observations for the i-th individual, where $i=1,\ldots,N$, and let the model be described by $F(\theta_i,\xi_i)$. Then:

$$y_i = f(\theta_i,\xi_i) + \epsilon_i(s + tf(\theta_i,\xi_i))$$

where $\xi_i=(x_{i1},\ldots,x_{in_i})'$ is a $n_i$-vector of explanatory variables for the individual i, $\theta_i$ is the p-vector of individual parameters and $\epsilon_i$ is the $n_i$-vector of random errors.

Here $\epsilon$ is normally distributed with zero mean and a diagonal variance matrix characterized by parameters s and t so that s relates to the additive error component while t relates to the multiplicative error component.

Where $\theta_i$ is defined by $\beta+b_i$, $\beta$ is the vector of fixed effects and b is the vector of random effects for individual i. Here $b_i$ is normally distributed with mean zero and variance $\Omega$.

The covariates for individual i is denoted by the vector $x_i$, and $\theta_i$ is defined by $g(\beta,b_i,x_i)$, where g is a known function. $\Psi$ is an estimate of a vector of all population parameters, let $\gamma$ be the vector of all variance terms. Then, $\Psi'=[\beta',\gamma']$ The Fisher information matrix for a population design $$M(\Psi,\Xi) = \sum_{i=1}^{N} M(\Psi,\xi_i),$$

where $\Xi=\{\xi_1,\ldots,\xi_N\}$ and $\xi_i$ is the ith individual design.

The Fisher information matrix for given values of x is given by:

$$E_{y|x}\left[-\frac{\partial^2 l(\theta;y)}{\partial\theta\partial\theta'}\right] \quad (6)$$

where $l(\theta;y)$ is the log-likelihood of observations y for the population parameters $\theta$. Due to the nonlinearity of f with respect to $\theta$, there is no analytical expression for $l(\theta;y)$. That is, in general, for say N individuals where Y is a matrix of responses for the whole population and $y_i$ is the vector of responses for the ith individual, the likelihood can be expressed as:

$$L(\beta; Y \mid x, \Omega) = \prod_{i=1}^{N} L\left(\beta; y_i \mid x_i, \omega_i\right) \quad (7)$$

where $$L(\beta; y_i \mid x_i, \omega_i) = \int L(\beta; y_i; b_i \mid x_i, \omega_i) db_i \quad (8)$$

$$= \int L(\beta; y_i \mid b_i, x_i) L(b_i; w_i) db_i$$

Given the nonlinearity of $b_i$ in f, this integral is generally intractable. One solution for this integral is to approximate the nonlinear function with a first order Taylor expansion around the expected values of the random effects. The model is therefore:

$$y \cong f(g(\theta, \bar{v}, x), \xi) + \frac{\partial f(\theta, \bar{v}, x), \xi}{\partial v'}(v - \bar{v}) + \varepsilon(s + tf(g(\theta, \bar{v}, x), \xi)) \quad (9)$$

Then the log-likelihood l is approximated by:

$$-2l(\theta; y) \cong n \ln 2\pi + \ln|V| + \sum (y_i - E_i)' V^{-1}(y_i - E_i) \quad (10)$$

where E and V are the marginal expectation and variance of y given by:

$$E = E(y \mid x) \cong f(g(\beta, \bar{v}, x), \xi) - \frac{\partial f(g(\beta, \bar{v}, x), \xi)}{\partial v'} \bar{v}$$

$$V = \mathrm{Var}(y \mid x)$$
$$= \left[\frac{\partial f(g(\beta, \bar{v}, x), \xi)}{\partial v'}\right] \Omega \left[\frac{\partial f(g(\beta, \bar{v}, x), \xi)}{\partial v'}\right]' +$$
$$\mathrm{diag}(s + tf(g(\beta, \bar{v}, x), \xi))^2$$

Then the Fisher information matrix can be expressed as:

$$M(\Psi, v, x, \xi) = \frac{1}{2} \begin{bmatrix} A(E, V) & C(E, V) \\ C'(E, V) & B(E, V) \end{bmatrix} \quad (11)$$

where $$A(E, V)_{mn} = 2\frac{\partial E'}{\partial \beta_m} V^{-1} \frac{\partial E}{\partial \beta_n} + tr\left(\frac{\partial E'}{\partial \beta_n} V^{-1} \frac{\partial E}{\partial \beta_m} V^{-1}\right),$$

for $m$ and $n = 1, \ldots, dim(\beta)$ $$B(E, V)_{mn} = tr\left(\frac{\partial V}{\partial \gamma_m} V^{-1} \frac{\partial V}{\partial \gamma_n} V^{-1}\right),$$

for $m$ and $n = 1, \ldots, dim(\gamma)$ $$C(E, V)_{mn} = tr\left(\frac{\partial V}{\partial \gamma_m} V^{-1} \frac{\partial V}{\partial \beta_n}\right),$$

for $m = 1, \ldots, dim(\beta)$ and $n = 1, \ldots, dim(\gamma)$

Thus, the approximate expected information matrix for a nonlinear mixed effects model is formed. This can now be used in a variety of optimality criteria to form designs with desired properties.

Bioelectrical Impedance Study

The application of these techniques to Bioelectrical impedance analysis (BIA), as modeled using the Cole equation, will now be explained. In particular D-optimal designs are derived based on different assumptions about the interaction between frequency and impedance and also the practical limitations of such a study.

This is achieved by obtaining initial parameter estimates by modeling data on individuals, using these initial estimates to form D-optimal designs and then extending these D-optimal designs so that they perform well in practice.

Optimal Designs for Studying Bioimpedance

In this example the Fisher information matrices are determined using the software package POPT written by S. B. Duffull. The search routine uses an adapted version of a simulated annealing algorithm for continuous variables. Together these techniques provide a means of finding D-optimal designs for nonlinear mixed and fixed effects models across a continuous search space.

Modeling the Data

For the Cole equation, initial parameter estimates were found by modeling paired frequency and bioimpedance data on 61 subjects. Whole-body, wrist to ankle, multifrequency bioimpedance data were recorded over the frequency range 5 to 1024 kHz using an Impedimed-SEAC SFB3 tetra-polar impedance instrument.

Modelling was performed using the software package MONOLIX, which is a MATLAB based package that uses stochastic approximation to the expectation maximization (SAEM) algorithm, in parametric maximum likelihood estimation for nonlinear mixed effects models.

The Expectation-Maximization (EM) algorithm is an iterative procedure used for likelihood function maximization given incomplete data sets formed from observable and non observable data. The E-step in this algorithm cannot be performed in closed formed due to the nonlinearity in f of the random effects, as described above.

The SAEM algorithm replaces this step with a stochastic procedure. Thus, the usual EM algorithm computes, at the kth iteration, the conditional expectation of the log-likelihood giving $Q_k(\Psi) = E[\log p(y, b_i; \Psi) | y, \Psi_{k-1}]$, where $p(y, b_i; \Psi)$ is the likelihood of $(y, b_i)$.

The SAEM replaces this step by drawing $b_i^{(k)}$ from the conditional distribution $p(\cdot | y; \Psi_k)$ and updates $Q_k(\Psi)$ as follows:

$$Q_k(\Psi) = Q_{k-1}(\Psi) + \delta_k(\log p(y, b_i^{(k)}; \Psi) - Q_{k-1}(\Psi))$$

where $\delta_k$ is a decreasing sequence of positive numbers.

To fit a nonlinear model to data, initial parameter estimates are also needed. For this model, initial estimates of fixed effects were taken from previous studies, and estimates of variance were found by what is called a 'Standard Two Stage Approach'. This involves estimating fixed effects for all data specific to each individual. Then, the variance of these estimates is calculated and used as an estimate for $\Omega$.

Figure 6:
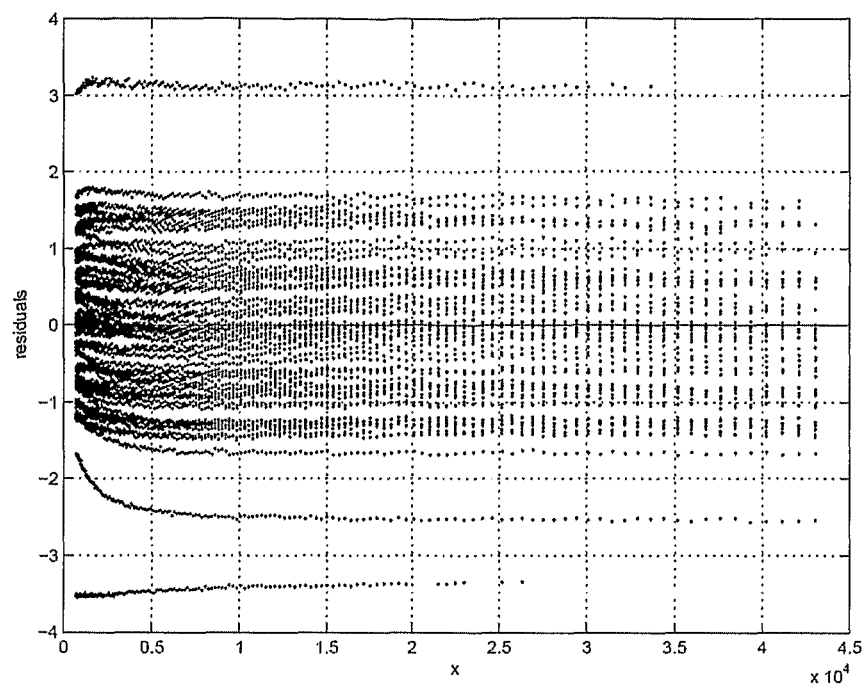
FIG. 6 is an example of a residual plot for determining an initial model fit.

The first stage of the modeling process was to find a suitable residual variance model such that the residuals are normally distributed around zero so that tests, such as the likelihood ratio test, are valid. Given the initial estimates, the first run uses a diagonal variance-covariance matrix with all four parameters having a normally distributed random component and the model having additive residuals. The residual plot is shown in FIG. 6.

This shows that the assumption about additive variance holds reasonably well and the residuals are centered around zero. Whilst the plot is not completely random at low frequencies, due for example to technical errors of measurements and inaccuracies associated with using the Cole equation to model bioelectrical impedance, this is considered acceptable.

This additive variance model can then be compared with the multiplicative and additive plus multiplicative error models. The residual plot was best when the additive error model was used.

The initial model can then be compared with different models having various fixed effects parameters. For example, the initial model can be compared with a model setting the parameter c to have no random component to it, that is having a fixed effect only. The likelihood ratio test for nested models can then be used to compare these models with the initial run. In this instance it was found that the initial run significantly increased the log-likelihood to justify having all parameters in the model.

The final step of the modeling process is to allow some or all of the random effects to have a log-normal distribution. This shows that found parameter estimates were not biologically plausible and can therefore be disregarded.

In the end, the initial model chosen to start the modeling process was the one chosen based on the above reasoning. It was also the model that provided the maximum value of the log-likelihood of (y; θ).

Using the model described above, the final estimates can be found in table 1, where the random effects are normally distributed around zero with variance SZ; a diagonal matrix with diagonal elements $[\omega_1^2, \ldots, \text{and } \omega_4^2]$ is the residual variance.

TABLE 1

| Parameter | Estimate (CV %) |
|---|---|
| $R_0$ | 861.00 (2.04) |
| $R_{inf}$ | 320 (1.58) |
| C | 2.4e−006 (2.08) |
| α | 0.649 (1.07) |
| $\omega_1^2$ | 1.92e+004 (18.39) |
| $\omega_2^2$ | 1.66e+003 (19.04) |
| $\omega_3^2$ | 1.64e−013 (19.27) |
| $\omega_4^2$ | 0.00302 (16.39) |
| $s^2$ | 5.46 (0.93) |

It will be appreciated that these values are derived from actual physical measurements and will therefore depend on collected data. The above values are therefore for the purpose of illustration only and are not intended to be limiting.

A coefficient of variation (CV %) is calculated by dividing the standard error of an estimate by its estimate and multiplying this by 100 to form a percentage. Typically, acceptable CV %'s for fixed parameters and random parameters are 20% and 50%, respectively. From the table 1, we can see that the CV %'s for our estimates are more than reasonable.

D-Optimal Design for Fixed Effects Model

Examining a design for one individual using the fixed effects model will now be described using the initial estimates found in the previous section, $\theta=[R_0, R_{inf}, C, \alpha]'=[861, 320, 2.4e-006, 0.649]'$. The design which maximises the determinant of the information matrix is:

$$\xi_{D^*_{fixed}} = \begin{Bmatrix} 0.0001 \\ 3.7357 \\ 31.8801 \\ 1000.0000 \end{Bmatrix}$$

However, as described above, this is for the values shown in Table 1 and if different values are used, a different matrix will be determined.

D-optimality generally selects extreme values of covariates, but this also occurs to an extent due to the nature of the Cole equation. If $\bar{\omega}$ approaches zero, the Cole equation will approach $Z=R_0$. Alternatively, if $\bar{\omega}$ approaches infinity $Z=R_\infty$. Thus, extreme frequencies provide simpler expressions for $R_0$ and $R_\infty$.

The calculation of the D-efficiency will be described below, providing an indication of the limitation of not accounting for between subject variability seen in the next section.

Mixed Effects

For the Cole equation, parameter estimates are known to vary between subjects, and accordingly a mixed effects model must be used.

For the purpose of this analysis it will be assumed that it is possible to administer electrical currents through the body at frequencies [0, 1000] kHz, and obtain an accurate reading of bioelectrical impedance Thus, this can assume a model:

$$y_i = f(\theta, \xi) + s\epsilon_i \quad (15)$$

Using the initial estimates from the fixed effects model determined above, and shown in table 1, the following D-optimal design was found by maximizing the determinant of equation 11:

$$\xi_{D^*_{add}} = \begin{Bmatrix} 0.0001 \\ 5.0374 \\ 77.4409 \\ 1000.0000 \end{Bmatrix}$$

When forming the expected fisher information matrix for this design, C(E, V) is set to a block matrix of zeros. Then, under this assumption, the fixed and random effects of the model are independent.

The D-efficiency of the fixed effect design under the mixed effects model is 0.9692. Such a high efficiency of the fixed effects D-optimal design suggests that, in this case, accounting for between subject variance only marginally improves the ability to estimate the parameters of the Cole equation.

Dealing with Practical Limitations

With bioelectrical impedance studies, it is known that low and high frequencies produce more highly variable readings of bioimpedance compared with less extreme frequencies.

Two possible approaches to account for this variability will now be described. The first restricts the design space to exclude frequencies where readings of bioimpedance are inaccurate. The second allows the residual variance to depend on the frequency in some manner that mimics real life patterns.

D-optimal Design with Restricted Frequencies

The straight forward approach to dealing with such a variance structure is to avoid frequencies which produce highly variable bioimpedance measures. At present, such bioimpendance studies limit the frequencies to being between a variety of ranges due to this added variability. Examples of such ranges are [4, 200], [4, 500] and [4, 750]. These intervals, therefore are used to define restricted designs.

Allowing parameters to vary between individuals the following D-optimal designs were found for the above example:

TABLE 2

| Range | Frequency | D-eff under Mixed Effects Design |
|---|---|---|
| [4, 200] | 4.0000 | 0.4320 |
|  | 15.1909 |  |
|  | 60.4311 |  |
|  | 200.0000 |  |
| [4, 500] | 4.0000 | 0.5977 |
|  | 18.8903 |  |
|  | 114.7364 |  |
|  | 500.0000 |  |
| [4, 750] | 4.0000 | 0.06752 |
|  | 21.5242 |  |
|  | 143.0364 |  |
|  | 750.0000 |  |

The D-efficiencies of these restricted designs under the mixed effects models are also shown in table 2. As the range becomes more restricted, the efficiencies decrease. This is highlighted by the D-efficiencies of these designs, which suggest that, under the assumption of constant additive variance, restricting the frequencies to certain intervals creates a significant loss in our ability to estimate parameters precisely. Consequently we will be forced to sample more often in the restricted case to obtain as precise estimates as in the unrestricted case.

D-optimal Design with Variance Function

An assessment of the preferred model can be made by adding a variance function into the model that mimics the variance of bioimpedance in real life studies.

In this case, once the true variance structure has been captured by the function, the D-optimal design will provide the best estimates of the parameters. Inherent in this design will be the ideal range to restrict our frequencies, based on the variance function used.

To achieve this, a model of the following form is used:

$$y_i = f(\theta_i, \xi_i) + \epsilon_i(s_1 + s_2 h(\xi_i)) \quad (16)$$

where $h(\xi_i)$, a function of frequency, specifies the variance function.

Relaxing the assumption about constant variance of the residuals by forming a variance function described above, allows accurate capture and mimicking of the residual structure, without violating any nonlinear regression assumptions.

Figure 7:
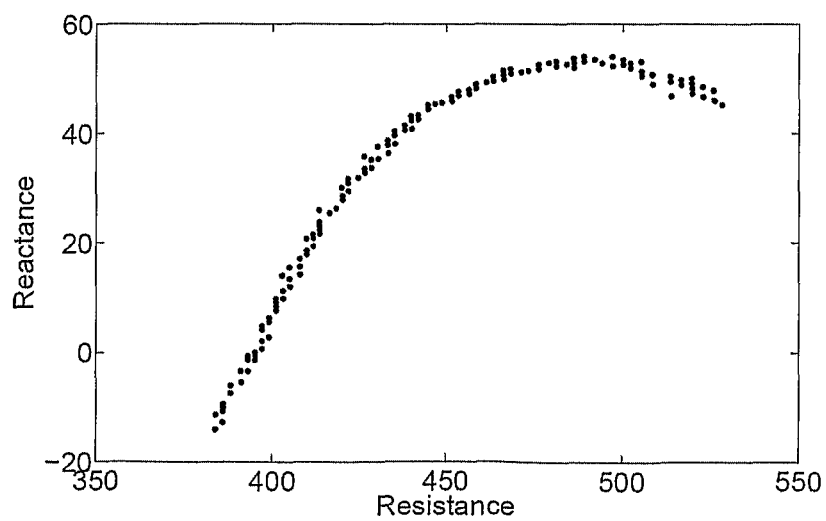
FIG. 7 is an example of a resistance versus reactance plot for example impedance measurements.

Bioimpedance is made up of two parts, resistance and reactance, relating to the real and imaginary parts of the Cole equation, respectively. An example plot of resistance vs reactance is shown in FIG. 7. This plot is of real data and as such shows the real life deviations from the theoretical semi-circle that would be produced from the pure circuit seen in FIG. 4.

The peak of the locus of the semi-circle identifies the characteristic frequency $f_c$. This frequency yields the smallest variance due to the variance function and consequently, it is assumed that at this frequency the constant additive variance dominates. The variance function needs to be such that there is relatively small variance between the chosen interval, for example [4, 750], with rapidly increasing variance for frequencies outside these bounds.

Accordingly, a double exponential model, centred around $f_c$, can be used to adequately model the variance of such a study. Thus, for the range 0 kHz to 1000 kHz, frequencies between $f_c$ and 1000 are rescaled to be between 0 and 1. Similarly, frequencies between 0 and $f_c$ are rescaled so that they are between 1 and 0. The new vector of rescaled frequencies is then exponentiated twice, and scaled such that the vector has a minimum and a maximum at 0 and 1, respectively. Finally, slightly extra variability is added to frequencies greater than $f_c$ by multiplying the resealed numbers which relate to these frequencies by 2. This whole vector is then multiplied by $\sigma_{extra}^2$.

Figure 8:
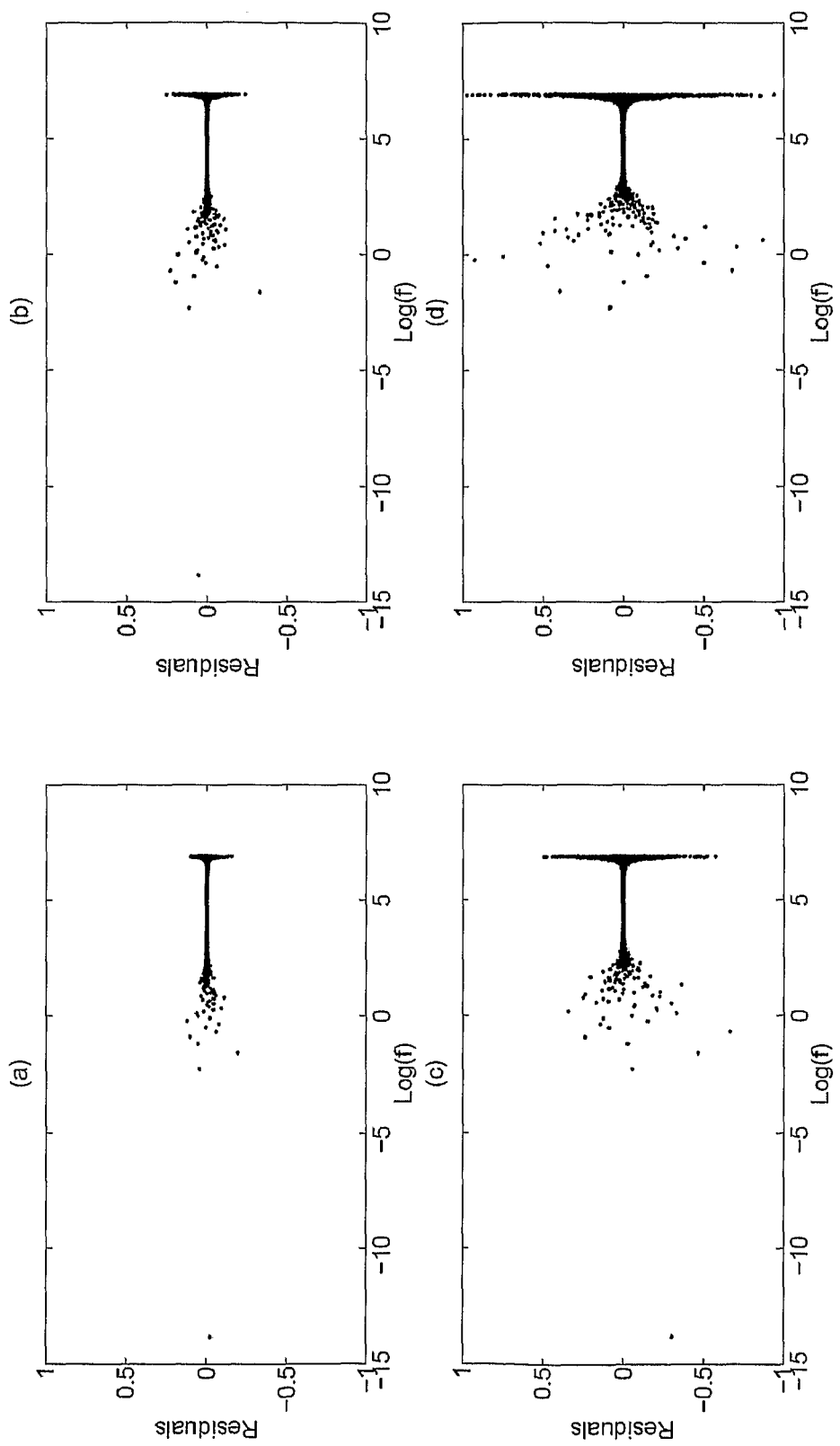
FIG. 8 is an example of plots of a variance function for various values of $\sigma^2$; and, FIG. 9 is an example of a plot of residuals from a model fit using an example extracted data set.

Example residual plots of this variance function $h(\xi)$ for various $\sigma_{extra}^2$ values are shown in FIG. 8. In order to illustrate the variation of impedance at small frequencies, the log of frequency is shown in all four plots.

From this it can be seen that the actual structure of the function does not change, but is merely at a different scale. This also shows how variable readings of bioimpedance can be at low and high frequencies, particularly when $\sigma_{extra}^2$ is large, and how there exists relatively small variance between 4 and 750.

This leads to another consideration for this variance structure, in particular, how much should bioimpedance vary at low and high frequencies, and therefore how large should $\sigma_{extra}^2$ be such that it will capture the real life variance structure of bioimpedance.

Table 3 shows D-optimal designs found for various values of $\sigma_{extra}^2$. The D-efficiencies shown refer to the efficiency of each design compared with the D-optimal design described above. For all designs, the model considered is from equation 16.

TABLE 3

| $\sigma_{extra}^2$ | $\xi_D^*{}_{multi}$ | D-eff |
|---|---|---|
| 0 | 0.0001 | 1.0000 |
|  | 5.0371 |  |
|  | 77.4409 |  |
|  | 1000.000 |  |
| 0.1 | 0.0001 | 0.6837 |
|  | 15.3454 |  |
|  | 109.5900 |  |
|  | 699.9127 |  |
| 0.2 | 14.6420 | 0.6383 |
|  | 59.5391 |  |
|  | 186.4495 |  |
|  | 680.5794 |  |
| 0.5 | 20.6291 | 0.5831 |
|  | 68.7527 |  |
|  | 183.2815 |  |
|  | 595.1341 |  |
| 1 | 25.7367 | 0.5409 |
|  | 74.3527 |  |
|  | 175.7765 |  |
|  | 530.8203 |  |

This shows that as the variance increases at the low and high frequencies, the criterion starts to choose frequencies at the less extreme values, thereby avoiding regions which relate to a highly variable reading of bioimpedance. Thus, it is up of the experimenter to decide how variable bioimpedance can be. Once this is decided, the D-optimal design will take this variability into account and find the design which will give the best estimates of parameters.

For example, at a first instance, a broad set of preferred frequency ranges can be defined as follows:
 0-50 kHz;
 2-200 kHz;
 50-500 kHz; and,
 200-1000 kHz.

However, using a more limited design space based on the above mentioned practical constraints can lead to more specific frequency ranges as follows:
 0-24 kHz;
 5-74 kHz;
 77-200 kHz;
 530-1000 kHz.

In a more extreme limitation, for example, assuming $\sigma^2=0.2$ is a true representation of the variance, then the optimal design can be seen in the above table, indicating that measurements at frequencies lower than 14.64 kHz and higher than 680.60 kHz are too variable and should be avoided.

Uncertainty in Prior Estimates

Inaccurate prior estimates of parameters for nonlinear models can lead to designs that have a limited ability to estimate parameters that diverse considerably from what was expected. In order to find a design that offers efficient parameter estimates across a wide range of prior estimates, we can look at product design optimality discussed above.

A product design is generally more robust to changes in initial parameter estimates than local D-optimal designs for each parameter set. Thus, a product design is preferred if uncertainty exists in the initial parameter estimates.

Product Design

Given the initial parameters estimates above, 5th and 95th percentiles of the population can be found using the estimates of the between subject variability. For example, given the initial estimate of $R_0=861$ with $\omega_1=138$, the 5th and 95th percentiles would be 584 and 1138, respectively.

Such percentiles can be determined for all four model parameters giving a set of eight different initial estimates which would be used as eight different impedance models in the product design. The eight parameter sets considered can be seen in table 4.

TABLE 4

| Model | $R_0$ | $R_{inf}$ | C | α |
|---|---|---|---|---|
| 1 | 1138 | 370 | 2.40e−06 | 0.6490 |
| 2 | 584 | 370 | 2.40e−06 | 0.6490 |
| 3 | 861 | 401 | 2.40e−06 | 0.6490 |
| 4 | 861 | 239 | 2.40e−06 | 0.6490 |
| 5 | 861 | 320 | 3.21e−06 | 0.6490 |
| 6 | 861 | 320 | 1.59e−06 | 0.6490 |
| 7 | 861 | 320 | 2.40e−06 | 0.7589 |
| 8 | 861 | 320 | 2.40e−06 | 0.5391 |

The product design is formed by optimizing over the product of the determinants of the respective variance-covariance matrices of the eight models as a single function. The idea behind forming product designs in this way is that optimizing across all eight models will provide a design which is efficient across a wide range of parameter estimates. The model considered is of the form of equation 16 ($\sigma_{extra}^2=0.2$), the values for which are set out in Table 3 as:

$$\xi_{D^*_{multi}} = \begin{Bmatrix} 14.6426 \\ 59.5391 \\ 186.4495 \\ 680.5794 \end{Bmatrix}$$

The following product design is given by:

$$\xi_{(D_1,\dots,D_8)^*_{multi}} = \begin{Bmatrix} 14.1844 \\ 56.9201 \\ 187.5397 \\ 679.1141 \end{Bmatrix}$$

Design Evaluation

To analyze how efficient the product design is at estimating parameters across all models, the efficiency of the design under each model is determined, as shown in table 5, in which the efficiency of the product design is compared to each D-optimal design for each parameter set.

TABLE 5

| Model | D-eff |
|---|---|
| 1 | 0.9923 |
| 2 | 0.9932 |
| 3 | 0.9890 |
| 4 | 0.8129 |
| 5 | 0.9573 |
| 6 | 0.7298 |
| 7 | 0.9982 |
| 8 | 0.9997 |

The efficiency of the product design can be calculated by comparing its D-value under each model compared to the D-optimal value under the respective model. Table 5 shows the efficiency of the product design compared to each D-optimal design for each parameter set. Relatively high efficiencies across all models suggest that the product design is a good means for allowing for uncertainty in initial parameter estimates. Further, given the range of parameter values considered, it is believed that these designs will efficiently estimate model parameters for a variety of individuals. Hence, this approach and the frequencies found should benefit bioimpedance analysis.

A practical approach, applies real data to determine how well model parameters can be estimated. Given the design:

$$\xi_{(D_1,\dots,D_8)^*_{multi}} = \begin{Bmatrix} 14.1844 \\ 56.9201 \\ 187.5397 \\ 679.1141 \end{Bmatrix}$$

and the data on 61 individuals, impedance at these frequencies were extracted from the data set of all individuals and a nonlinear mixed effects model was fitted to this extracted data set.

Using the same model and initial parameter estimates as discussed in the modelling section above, MONOLIX provides estimates for the parameter values as shown in table 6 and estimates of coefficients of variation found in table 7.

TABLE 6

| Parameter | Full Data Set | Extracted Data Set |
|---|---|---|
| $R_0$ | 861 | 879 |
| $R_{inf}$ | 320 | 303 |
| C | 2.4e−006 | 3.25e−006 |
| α | 0.649 | 0.68 |
| $\omega_1^2$ | 1.92e+004 | 1.1e+04 |
| $\omega_2^2$ | 1.66e+003 | 1.52e+003 |
| $\omega_3^2$ | 1.64e−013 | 5.31e−012 |
| $\omega_4^2$ | 30.2e−003 | 1.37e−003 |
| $s^2$ | 5.46 | 5.24 |

Figure 9:
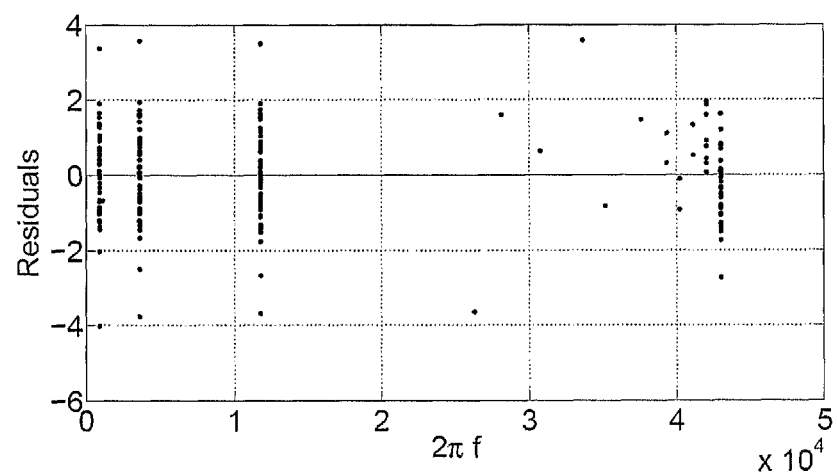

FIG. 9 shows the residual plot for this fit, indicating that the nonlinear regression assumptions discussed above hold.

The new estimates shown in table 6 are similar to those found using the full data set of observations. Given this and the residual plot, it is concluded that this D-optimal design performs well in practice and as such, with the use of only four frequencies, we have been able to form estimates of parameters of the Cole equation similar to those found by using the full data set.

It is also clear that the product design performs well in practice and requires of only four is frequencies per individual. That is, the optimal choice of these frequencies yields the ability to efficiently estimate model parameters. Further, it highlights the apparent lack of information gained by choosing over 100 unique frequencies per individual to model bioimpedance.

Table 7 shows that the coefficients of variation estimated from the full data set are similar to those estimated from the extracted data set. This suggests that only four measurements of impedance per individual are needed to efficiently estimate the parameters of the Cole equation.

TABLE 7

|  | Full Data Set | Extracted Data Set | Expected |
|---|---|---|---|
| $R_0$ | 2.04 | 1.76 | 4.15 |
| $R_{inf}$ | 1.58 | 2.51 | 6.33 |
| C | 2.08 | 11.11 | 14.24 |
| α | 1.07 | 1.57 | 4.74 |
| $w_1^2$ | 18.39 | 20.09 | 19.14 |
| $w_2^2$ | 19.04 | 22.04 | 42.18 |
| $w_3^2$ | 19.27 | 24.48 | 177.34 |
| $w_4^2$ | 16.39 | 28.69 | 36.82 |
| $s^2$ | 0.93 | 12.35 | 9.80 |

Table 7 also shows the expected coefficients of variation calculated by using the expected Fisher information matrix to form the expected standard errors of estimates.

Accordingly, this shows that experimental design for non-linear fixed and mixed effects models can be applied BIA, allowing preferred frequency measuring models to be determined. Numerous four frequency designs were found relating to D-optimal designs based on various assumptions about how frequency relates to bioimpedance and how parameters vary between individuals. Product designs were also found. These designs should be robust to changes in initial estimates.

D-optimal designs can also be applied to real data where it was shown to perform well against the full data set. It is hoped that the D-optimal design approach used here and the designs found will aid BIA researchers in the design of optimised multiple frequency BIA instrumentation. This will mitigate the acknowledged inadequacy of some currently used instrumentation and provide for better clinical utility, for example, the accurate prediction of lean body mass for drug dosing in the obese.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A method of measuring the impedance of a subject, the method including, in a measuring device including a processing system:
   a) causing one or more electrical signals to be applied to the subject using a first set of electrodes, the one or more electrical signals having four frequencies;
   b) measuring electrical signals across a second set of electrodes applied to the subject in response to the applied one or more signals;
   c) determining from the applied signals and the measured signals at least one measured impedance value at each of the four frequencies, wherein the four frequencies are:
      i) 14 kHz;
      ii) 57 kHz;
      iii) 188 kHz; and,
      iv) 679 kHz.

2. A method of measuring the impedance of a subject, the method including, in a measuring device including a processing system:
   a) causing one or more electrical signals to be applied to the subject using a first set of electrodes, the one or more electrical signals having four frequencies;
   b) measuring electrical signals across a second set of electrodes applied to the subject in response to the applied one or more signals;
   c) determining from the applied signals and the measured signals at least one measured impedance value at each of the four frequencies, wherein the four frequencies are:
      i) 14.1844 kHz;
      ii) 56.9201 kHz;
      iii) 187.5397 kHz; and,
      iv) 679.1141 kHz.

3. A method according to claim 1, wherein the method includes determining one or more impedance parameter values based on the plurality of measured impedance values.

4. Apparatus for measuring the impedance of a subject, the apparatus comprising:
   a first set of electrodes;
   a second set of electrodes; and
   a processing unit;
   wherein the processing unit is configured to:
   a) cause one or more electrical signals to be applied to the subject using the first set of electrodes, the one or more electrical signals having four frequencies;
   b) measure electrical signals across the second set of electrodes applied to the subject in response to the applied one or more signals; and
   c) determine from the applied signals and the measured signals at least one measured impedance value at each of the four frequencies, wherein the four frequencies are:
      i. 14 kHz;
      ii. 57 kHz;
      iii. 188 kHz; and
      iv. 679 kHz.

5. Apparatus according to claim 4, the measuring device including:
   a) a current source for applying current signals to the subject;
   b) a voltage sensor for measuring voltages signals across the subject; and,
   c) the processing system coupled to the current source and the voltage sensor for:
      i) causing the current signals to be applied to the subject; and,
      ii) determining the impedance using the applied current signals and measured voltage signals.

6. Apparatus for measuring the impedance of a subject, the apparatus comprising:
   a first set of electrodes;
   a second set of electrodes; and
   a processing unit;
   wherein the processing unit is configured to:
   a) cause one or more electrical signals to be applied to the subject using the first set of electrodes, the one or more electrical signals having four frequencies;
   b) measure electrical signals across the second set of electrodes applied to the subject in response to the applied one or more signals; and c) determine from the applied signals and the measured signals at least one measured impedance value at each of the four frequencies, wherein the four frequencies are:
   i. 14.1844 kHz;
   ii. 56.9201 kHz;
   iii. 187.5397 kHz; and
   iv. 679.1141 kHz.

* * * * *